United States Patent [19]
Bartish

[11] 4,131,568
[45] Dec. 26, 1978

[54] CATALYTIC SYNTHESIS OF LOW MOLECULAR WEIGHT HYDROCARBONS

[75] Inventor: Charles M. Bartish, Bethlehem, Pa.

[73] Assignee: Air Products and Chemicals, Inc., Allentown, Pa.

[21] Appl. No.: 604,633

[22] Filed: Aug. 14, 1975

[51] Int. Cl.$^2$ .................. B01J 29/06; C07C 27/06
[52] U.S. Cl. .................. 252/455 Z; 260/449.6 R
[58] Field of Search ............ 252/454, 455 Z, 459, 252/474

[56] References Cited
U.S. PATENT DOCUMENTS

| | | | |
|---|---|---|---|
| 2,628,969 | 2/1953 | Rottig | 252/474 X |
| 3,507,931 | 4/1970 | Morris et al. | 252/455 Z |
| 3,759,825 | 9/1973 | Chun et al. | 252/459 X |

Primary Examiner—Carl Dees
Attorney, Agent, or Firm—Russell L. Brewer

[57] ABSTRACT

This invention relates to an improvement in a Fischer-Tropsch catalytic process for synthesizing a hydrocarbon stream and to the resulting catalyst. The improvement for synthesizing a high percentage of $C_2$–$C_4$ hydrocarbons and obtaining excellent conversion percentages comprises conducting said reaction at a temperature of from about 275° to 375° C, a pressure of from about 75 to 350 psi, a space velocity of about 50 to 400 hours$^{-1}$ in the presence of a catalyst comprising from about 100 to 1 parts iron per part copper, the catalyst being carried on a support selected from the group consisting of a zeolite, silica-alumina and mixtures thereof.

4 Claims, No Drawings

CATALYTIC SYNTHESIS OF LOW MOLECULAR WEIGHT HYDROCARBONS

BACKGROUND OF THE INVENTION

The Fischer-Tropsch catalytic synthesis of both gaseous and liquid hydrocarbon streams by hydrogenating carbon monoxide has been the subject of considerable research from about 1920 to about 1960. Early work primarily related to the generation of liquid hydrocarbons and particularly to the synthesis of gasoline, kerosene and diesel fuel. Later, some emphasis was placed on the synthesis of low molecular weight hydrocarbons other than methane e.g. low molecular weight paraffins, olefins and oxygenated compounds e.g. low molecular weight alcohols, aldehydes, ketones and acids.

In recent years, because of crude oil shortages, price increases and the tremendous demand for polymeric products generated from low molecular weight hydrocarbons, impetus has been provided for synthetically generating low molecular weight hydrocarbons from alternate sources e.g. coal. This is particularly true for those countries not having oil-producing capabilities, but having huge supplies of coal or other fuel sources as this would relieve them from some of the dominance exercised by oil producing countries.

DESCRIPTION OF THE PRIOR ART

In U.S. Pat. No. 2,973,384 it has been proposed to generate ethylene by hydrogenating carbon monoxide in the presence of alumina gel, silica gel, and optionally with a metal comprising copper, nickel, and cobalt. Efforts made in an attempt to duplicate the results i.e. the generation of large quantities of ethylene with conversions of 90% or above with respect to the carbon monoxide have resulted in failure.

In U.S. Pat. No. 2,717,259 there is disclosed a process for generating low molecular weight hydrocarbons by passing carbon monoxide and hydrogen through an iron or iron-copper catalyst which has been deactivated by a halogen as ethylene dichloride. The percentage of $C_2$ to $C_4$ paraffins obtained was about 10 to 25% with the percentage of olefins being about 25 to 45%. Some of the problems associated with the process include continuous addition of deactivating agent and precise control to prevent complete deactivation.

In U.S. Pat. No. 2,847,488 there is disclosed a process for synthesizing hydrocarbons and oxygenated compounds by hydrogenating carbon monoxide in the presence of an iron copper catalyst promoted with a small amount of potassium.

In U.S. Pat. No. 2,773,085 there is shown a process for producing oxygenated compounds by reacting a synthesis gas having a 1.5:2 molar ratio of hydrogen to carbon monoxide in the presence of an iron-copper catalyst supported on kieselguhr.

In U.S. Pat. No. 3,833,634 there is disclosed a process for preparing ethylene glycol by hydrogenating carbon monoxide using a rhodium complex catalyst e.g. rhodium dicarbonyl acetyl acetonate. The catalyst can be supported on a variety of catalyst supports e.g. kieselguhr, silica gel, silica-alumina and zeolites but preferably is employed as a homogeneous catalyst.

It has also been reported by Ralek et al. in Chem Abstract 77,66589V (1972) that gaseous hydrocarbons can be prepared by hydrogenating carbon monoxide in the presence of a catalyst e.g. iron or cobalt supported on a zeolite molecular sieve. Ralek et al. obtained small proportions of methane e.g. about 34%, while obtaining significant portions of ethane (26%), propane (26%) and butane (14%). However, yields of 8 to 19% based on the carbon monoxide were reported.

SUMMARY OF THE INVENTION

This invention relates to an improvement in a Fischer-Tropsch catalytic process for preparing low molecular weight hydrocarbons wherein a synthesis gas comprising carbon monoxide and hydrogen is passed through a catalyst bed under preselected conditions effective for reacting the carbon monoxide and hydrogen to form said hydrocarbons. The improvement for obtaining enhanced proportions of low molecular weight hydrocarbons while minimizing the proportion of methane produced and for obtaining enhanced conversions comprises conducting said reaction at a temperature of from about 275° to 375° C., a pressure of from about 75 to 350 psi, and a space velocity of from about 50 to 400 hours$^{-1}$ in the presence of a catalyst comprising from about 100 to 1 parts iron per part copper, said catalyst carried by a support selected from the group consisting of a zeolite, silica-alumina and mixtures thereof.

The invention also relates to a catalyst comprising from about 100 to 1 parts iron per part copper carried by a support selected from the group consisting of a zeolite, silica-alumina and mixtures thereof. The catalyst is particularly effective for Fischer-Tropsch catalysis in the generation of low molecular weight saturated hydrocarbons in high yield from carbon monoxide and hydrogen.

Advantages of this invention include:
the ability to form low molecular weight ($C_2$ to $C_4$) hydrocarbons in high yield while minimizing the formation of methane from a gas comprising carbon monoxide and hydrogen which can be derived from a secondary fuel source;
the ability to form low molecular weight hydrocarbons in sufficient quantity for conversion into olefins by cracking thereby permitting the formation of valuable compositions useful in polymer chemistry; and
the ability to form low molecular weight hydrocarbons by a synthetic route thereby making available, to non-oil producing countries, valuable compounds useful in producing polymers.

DESCRIPTION OF THE PREFERRED EMBODIMENTS

According to this invention, two factors are particularly important in synthesizing low molecular weight hydrocarbons from carbon monoxide and hydrogen and they include the selection of the catalyst and support used for effecting hydrogenation of carbon monoxide and the process conditions under which the reaction is carried out.

With regard to the selection of catalyst, the catalyst comprises a mixture of iron and copper carried on a support selected from the group consisting of a zeolite, silica-alumina and mixtures thereof. The iron is present in a proportion of from about 100 to 1 parts by weight per part copper. Preferably from about 20 to 5 parts iron are employed per part copper.

Even though the type of support is important in obtaining desired catalysts, the proportion of iron and copper is also important. If the proportion of iron falls below about 1 part per part of copper (by weight), the proportion of methane in the hydrocarbon gas stream increases substantially. On the other hand, when the proportion of iron is increased above about 100 parts per part copper, then there is insufficient copper present in the catalyst system, and even though supported on a zeolite or silica-alumina support, the activity of the catalyst is diminished substantially. As a result the conversion of carbon monoxide to valuable hydrocarbon products is very low e.g. 8 to 20%. Of course better yields and product distributions are obtained when the proportion of iron is from about 20–5 parts per part copper.

The selection of catalyst in carrying out the hydrogenation of carbon monoxide is particularly important as it has been found that the combination of iron and copper carried on a zeolite or silica-alumina support provides for enhanced conversion of carbon monoxide to hydrocarbon products with favorable distribution to low molecular weight $C_2$ to $C_4$ hydrocarbons.

The selection of the support for the catalyst is also important in order to obtain high carbon monoxide conversion. Those supports employed are zeolites, silica-alumina or mixtures. As is known zeolites are crystalline, hydrated aluminosilicates of Group 1 and Group 2 elements particularly of the sodium, potassium, magnesium and calcium type. Structurally, the zeolites are "framework" aluminosilicates which are based on an infinitely extending three dimensional network of $AlO_4$ and $SiO_4$ tetrahedra linked to each other by sharing all of the oxygen atoms. Several zeolite types as they are commonly referred to in the art, are available because of the various components which can be used for making the zeolite and the various structures which can be present.

Examples of zeolites which can be used for practicing the invention and referred to by structure type include zeolite A, zeolite R, zeolite S, zeolite X, zeolite Y, zeolite HS, zeolite N-A and those types such as faujasite, analcime, mordenite, natrolite, and ferrierite. On these synthetic zeolites, zeolite Y and the ammonium-exchanged mordenite are preferred for practicing the invention. Further discussions on zeolite types and structure can be found in the book *Zeolite Molecular Sieves Structure, Chemistry and Use* by Donald W. Breck, published by John Wiley & Sons, Inc., 1974.

A silica-alumina support may be used in place of the zeolite provided that the silica-alumina support is the type that is a reaction product as opposed to a physical mixture of silica and activated alumina. Such supports are well known and typically are prepared by precipitating sodium silicate and sodium aluminate and calcining at high temperature. For good results the silica-alumina support has from about 70–95% silica.

In a preferred embodiment of the invention the support is a mixture of zeolite and silica-alumina. Generally from about 5–50% by weight zeolite (preferably from about 15–25%) is employed as a support. The addition of silica-alumina to the support gives enhanced catalyst life as compared to pure zeolite and yet provides good conversion of carbon monoxide and yield of product. Pure zeolite in the reactor tends to form by-products which can plug the reactor whereas the formation of by-products is minimized by the addition of silica-alumina to the support.

Although various catalyst systems comprising iron and copper and transitional metals e.g. cobalt and nickel promoted with an alkali metal or the like have been utilized in Fischer-Tropsch synthesis, such catalysts, even though employed under similar conditions result in reduced conversion of carbon monoxide to hydrocarbons, generally result in poor distribution of hydrocarbons in terms of the $C_2$ to $C_4$ compounds produced. On the other hand, iron-copper catalysts supported on conventional supports such as kieselguhr, silica, and activated alumina, result in producing a high proportion e.g. 50% or greater of methane. Methane is well suited as a fuel, but is unsuited for the generation of olefins used in producing polymers.

The catalysts of the invention typically are formed by first dissolving or dispersing iron and copper salts e.g. iron and copper chloride or nitrate in water, then precipitating the metal oxides, mixing the precipitate with the zeolite or silica-alumina support, filtering and drying. The catalysts then are heat treated at a temperature of about 100°–350° C. for 12–15 hours. The catalysts can also be prepared by forming an iron-copper mixture and reducing the mixture to a particle size of from about 1–300 microns and blending this with the zeolite or silica-alumina support followed by heat treatment. However, for reasons of efficiency and economy, preparation of the catalyst is achieved by the first technique as this enhances the ability to impregnate and lodge the iron-copper components into the interstices of the zeolite or silica alumina support.

The second essential factor in synthesizing low molecular weight hydrocarbons e.g. $C_2$ to $C_4$ hydrocarbons, while minimizing the quantity of methane and heavier hydrocarbons produced in the Fischer-Tropsch reaction is the selection of appropriate reaction conditions in terms of the ratio of hydrogen to carbon monoxide ($H_2$/CO), temperature, pressure, and space velocity.

It has been found through considerable experimental work that the molar ratio of hydrogen to carbon monoxide should be from about 1:1 to about 3:1 and preferably from about 1.9:1 to about 2.2:1. Higher concentrations of hydrogen in the feed stream tend to result in the formation of greater quantities of methane and lower ratios of $H_2$/CO give rise to higher quantities of oxygenated compounds and hydrocarbons of greater molecular weight.

In order to minimize the amount of methane and high molecular weight hydrocarbons e.g. $C_5$ and above as well as paraffin waxes, the conditions are selected so that there is sufficient time for the chain length of the hydrocarbons to grow in the reaction but short enough to inhibit long chain formation. To accomplish this the temperature is maintained at about 275° to 375° C. and preferably at about 300° to 350° C. in order to permit the reaction to occur. Higher temperatures in the reaction chamber generally result in compositions having lower molecular weight e.g. or result in the formation of low molecular weight aldehydes and alcohol.

The pressure in the reaction chamber is adjusted from about 100 to about 350 psi and preferably to about 200 to 250 psi. Generally, as the temperature of the reaction is increased e.g. toward 350° C., the pressure is increased in order to obtain enhanced yields of $C_2$ to $C_4$ hydrocarbons. If the temperature at the high end of the range specified then the percentage of methane formed in the reaction chamber generally increases. On the other hand as the temperature and pressure are reduced toward the lower end of the scale, greater quantities of $C_5$ and above hydrocarbons are produced.

The flow rate of gas e.g. hydrogen and carbon monoxide passed through the catalytic bed is regulated so that the space velocity is from about 50 to 400 hours$^{-1}$.

Preferably the space velocity is controlled to about 100 to 300 hours$^{-1}$. When the space velocity falls below about 50 hours$^{-1}$, then higher portions of liquid hydrocarbons e.g. $C_5$ and above are obtained. On the other hand, when the space velocity exceeds about 300 hours$^{-1}$ higher proportions of methane are obtained.

The following examples are provided to illustrate perferred embodiments of the invention and are not intended to restrict the scope thereof.

EXAMPLE I

An iron-copper catalyst solution was prepared by dissolving 134 grams of $FeCl_2.4H_2O$, 91 grams $Fe(NO_3)_3.9H_2O$ and 37 grams of $Cu(NO_3)_2.3H_2O$ in two liters of distilled water heated to 70° C. After the solution was formed, 60 grams of an ammonium-exchanged mordenite was added to the solution and blended therein. Then two liters of a 10% solution of sodium carbonate in water at a temperature of 90° C. was added to the mixture of iron and copper salts and the mordenite. The resulting mixture was stirred for two hours, the formed precipitate filtered and dried over night at 100° C.

EXAMPLE II

An iron-copper catalyst system was prepared in accordance with Example I except that no support was added to the solution of iron and copper salts. A nonsupported iron-copper catalyst similar to Example I was obtained.

EXAMPLE III

An iron-copper catalyst on a silica-alumina support was prepared by the procedure of Example I except that 60 grams of a silica-alumina powder having a particle size of about 50–150 microns and containing about 87% silica was added to the solution of iron and copper salts. Then the catalyst in the resulting mixture was precipitated by the addition of two liters of 10% sodium carbonate solution at 90° C. A catalyst comprising iron and copper on a silica-alumina support was recovered, washed and dried in the same manner as in Example I.

EXAMPLE IV

A 105g portion of $Co(NO_3)_2.6H_2O$ was dissolved in 250 ml of distilled water. Then a 50g portion of the ammonium-exchanged mordenite of Example 1 was added to the solution and blended therein. The water was evaporated by heating to a temperature of 110° C. for about a 12 hour period and then heating to 350° C. for about 12 hours thereby forming a catalyst comprising 30% cobalt on an ammonium exchanged zeolite.

EXAMPLE V

Seventy five grams of a silica-alumina support as described in Example III were dispersed in about 200 ml of water. Then 25 ml of a 0.153 molar solution of $RuCl_3.3H_2O$ was added to the dispersion and mixed therein. The water was removed by vacuum followed by heating to 110° C. for about 12 hours thereby forming a catalyst comprising 0.5% ruthenium on a silica-alumina support.

EXAMPLE VI

An iron-copper catalyst on a Y type zeolite having a magnesium cation (MgY) was prepared in accordance with Example I except that the MgY type zeolite was substituted for the ammounium-exchanged mordenite.

EXAMPLE VII

A catalyst comprising iron and copper on a mordenite type zeolite having a magnesium cation (Mg-mordenite) was prepared in accordance with Example I except that a Mg-mordenite zeolite was substituted for the ammonium-exchanged mordenite.

EXAMPLE VIII

An iron-copper catalyst on ammonium Y type zeolite in combination with 80% of a silica-alumina support containing 87% silica was prepared in accordance with Example I except that the amonium Y type zeolite was substituted for the ammonium-exchanged zeolite.

EXAMPLE IX

Several tests were conducted in an effort to synthesize low molecular weight hydrocarbons from hydrogen and carbon monoxide by varying the catalysts, and support, some of which are described in Examples I through VIII, the temperature, pressure, and hydrogen-carbon monoxide ratio and space velocity. The reaction was carried out by passing hydrogen and carbon monoxide gases through a continuous flow reactor carrying a fixed bed of catalyst. The reaction products were analyzed for weight percentage of $C_1$ to $C_5+$ hydrocarbons produced. Typical results of the tests over a one month period are shown in Table I.

TABLE I

| Catalyst | T °C | P psia | Space Velocity | $H_2/CO$ | $C_1$ | $C_2$ | $C_3$ | $C_4$ | $C_5+$ | Conversion % CO |
|---|---|---|---|---|---|---|---|---|---|---|
| 1. 30% Co on $NH_4$ X zeolite | 250 | 97 | 290 | 2.3/1 | 82.6 | 10.0 | 7.4 | — | — | 5 |
| 2. 0.5% Ru on silica-alumina | 300 | 350 | 150 | 2.0/1 | 77.2 | 9.2 | 9.2 | 4.1 | 0.2 | 25 |
| 3. Fe-Cu and silica-alumina $NH_4Y$ | 300 | 100 | 200 | 2.0/1 | 32.2 | 19.2 | 25.2 | 18.4 | 5.0 | 65.9 |
| 4. Fe-Cu/silica-alumina | 350 | 350 | 263 | 2.0/1 | 43.9 | 24.4 | 16.1 | 7.6 | 8.0 | 91 |
| 5. Fe-Cu/MgY | 325 | 200 | 125 | 1.0/1 | 32.2 | 19.6 | 29.1 | 14.0 | 5.1 | 95 |
| 6. Fe-Cu/Mg-mordenite | 325 | 200 | 125 | 1.0/1 | 32.2 | 22.0 | 26.7 | 14.2 | 4.9 | 75 |
| 7. Fe-Cu/no support | 325 | 200 | 100 | 1.0/1 | 77.3 | 11.6 | 8.5 | 2.6 | — | 64 |

The results in Table I clearly show a higher proportion of $C_2$ to $C_4$ hydrocarbons with good conversion for the iron-copper catalyst systems on a zeolite support as indicated in runs 3, 5 and 6 and on a silica-alumina support as indicated in run 4. When the iron-copper catalyst was unsupported, a high concentrations of methane (77%) were obtained. Run 3 employing a mixture of zeolite and silica-alumina had enhanced catalyst life as compared to the pure zeolite support in runs 5 and 6. The catalysts in runs 5 and 6 had a tendency to plug the reactor.

EXAMPLE XII

An iron-copper catalyst on a sodium Y type zeolite was prepared in accordance with Example I except that a sodium Y type zeolite was substituted for the ammonium exchanged mordenite. The proportion of iron and copper remained the same. Carbon monoxide was then hydrogenated in the reactor described in Example I varying the temperature, pressure, ratio of hydrogen to carbon monoxide and space velocity. The results are shown in Table II.

TABLE II

| | Fe-Cu on NaY | | | |
|---|---|---|---|---|
| RUN | 1 | 2 | 3 | 1A |
| Temperature, °C | 325 | 325 | 325 | 325 |
| Pressure, psig | 200 | 200 | 200 | 200 |
| $H_2/CO$ | 1:1 | 1:1 | 1:1 | 1:1 |
| Space Velocity | 100 | 100 | 250 | 160 |
| Hydrocarbons wt. % | | | | |
| $CH_4$ | 28.37 | 28.81 | 46.90 | 27.58 |
| $C_2H_6$ | 23.53 | 26.10 | 23.21 | 22.72 |
| $C_3H_8$ | 31.78 | 31.09 | 21.16 | 27.35 |
| $C_4H_{10}$ | 16.30 | 13.97 | 8.70 | 22.33 |

The results in Table II show that very small fractions of methane were produced by the iron-copper catalyst-zeolite support system employed at the reaction conditions specified.

On the other hand, iron-copper catalysts on different supports e.g. Kieselguhr and activated alumina typically produce higher concentrations of methane e.g. 50–75% or oxygenated compounds as noted in Example 1 of U.S. Pat. No. 2,773,085.

What is claimed is:

1. A cataylst composition comprising from about 100 to 1 parts iron per part copper carried on a support containing at least 5%–50% zeolite.

2. The catalyst of claim 1 wherein said catalyst comprises from about 20 to 5 parts iron per part copper.

3. The catalyst of claim 2 wherein said zeolite in said support is an ammonium-exchanged mordenite.

4. The catalyst of claim 2 wherein said zeolite in said support is an ammonium Y zeolite and said support contains 15%–25% zeolite.